(12) United States Patent
Schäfer et al.

(10) Patent No.: US 6,572,622 B1
(45) Date of Patent: Jun. 3, 2003

(54) BONE PLATE

(75) Inventors: Bernd Schäfer, Eggstrasse 27, CH-6315 Oberägeri (CH); Henry Halm, Bissendorf (DE)

(73) Assignee: Bernd Schäfer, Oberägeri (CH)

( * ) Notice: Subject to any disclaimer, the term of this patent is extended or adjusted under 35 U.S.C. 154(b) by 246 days.

(21) Appl. No.: 09/686,892

(22) Filed: Oct. 12, 2000

(30) Foreign Application Priority Data

Oct. 18, 1999 (DE) .......................................... 199 50 270

(51) Int. Cl.[7] .............................................. A61B 17/56
(52) U.S. Cl. ............................. 606/69; 606/61; 606/73
(58) Field of Search .......................... 606/69, 72, 70, 606/71, 73, 61, 75, 77, 78; 411/185, 187, 188, 399

(56) References Cited

U.S. PATENT DOCUMENTS

| | | | | |
|---|---|---|---|---|
| 3,605,845 A | * | 9/1971 | Junker | 411/185 |
| 5,275,601 A | * | 1/1994 | Gogolewski et al. | 411/399 |
| 5,662,652 A | * | 9/1997 | Schafer et al. | 606/61 |
| 5,713,898 A | * | 2/1998 | Stucker et al. | 606/60 |
| 5,879,119 A | * | 3/1999 | Robinson | 411/188 |
| 6,406,478 B1 | * | 6/2002 | Kuo | 606/69 |

FOREIGN PATENT DOCUMENTS

| | | |
|---|---|---|
| DE | 44 33 360 | 2/1996 |
| DE | 4433360 | * 12/1996 |
| WO | WO 97 09 000 | 3/1997 |

* cited by examiner

Primary Examiner—Pedro Philogene
(74) Attorney, Agent, or Firm—Paul Vincent

(57) ABSTRACT

The invention concerns a bone plate which can be mounted to a vertebra. This is effected by bone screws which engage in the opening of the bone plate. At least one of the openings of the bone plate serves for receiving the screw head of the bone screw and is provided with a surface structure.

16 Claims, 1 Drawing Sheet

BONE PLATE

This application claims Paris Convention priority of DE 199 50 270.6 filed Oct. 18, 1999 the complete disclosure of which is hereby incorporated by reference.

BACKGROUND OF THE INVENTION

The invention concerns a bone plate for osteosynthesis, comprising a plate-shaped basic body and a lid, wherein the basic body comprises at least one opening for receiving a bone screw mounting same e.g. to a vertebra, in that the opening receives the screw head of the bone screw.

Bone plates are known per se. Bone plates of this type are e.g. mounted to vertebrae to stabilize same. For this purpose, the individual bone plates are connected to one another via rods, wherein the rods are mounted, in particular clamped, to the bone plates.

The bone plates are mounted to the vertebrae by means of bone screws which penetrate the bone plates and are screwed into the vertebrae. The bone plate is generally held by the screw head.

It has thereby turned out that the bone plate initially tightly abuts the vertebra, but may loosen with time, in particular if the bone screw loosens within the vertebra or if the bone changes in the abutment area of the bone plate.

It is therefore the underlying purpose of the invention to provide a bone plate which reduces the danger of subsequent loosening.

SUMMARY OF THE INVENTION

This object is achieved in accordance with the invention in that, in a bone plate of the initially described type, a surface structure is provided on at least a partial area of the opening surface facing the screw head.

The surface structure in the opening on which the screw head abuts results in a retaining effect, i.e. in a turning-out direction of the screw head. The bone plate is thus connected, both in frictional as well as in positive engagement, to the screw head and thus to the screw. The positive engagement reduces the danger that the screw loosens, i.e. loses the fixed support in the bone. There is furthermore a connection between screw head and bone plate even if the bone changes its shape in the abutment area of the bone plate.

In a preferred manner, the opening is circular. Such openings permit easy screwing-in and abutment of the screw head.

Although only part of the periphery of the opening must be provided with a surface structure, in a preferred embodiment, the surface structure extends over the entire inner circumference of the opening. This has the essential advantage that the head of the bone screw is also fixed over its entire outer periphery by anchoring it in the opening in positive engagement.

A further development provides that the area of the opening facing away from the bone comprises a surface structure. In particular, with a spherical cap-shaped opening, into which a spherical head of the bone screw is inserted, the nearly vertical i.e. less inclined area of the opening facing away from the bone is provided with the surface structure which renders the support of the screw head more secure than in the inclined area. In that area which is oriented essentially vertically to the screw axis, the screw head moves, during screwing-in of the screw, essentially parallel to and along the inner surface of the opening. Only near the end of the screwing-in process is the lower area of the screw head supported on the inclined section of the spherical cap-shaped opening to thereby retain the bone plate on the bone.

In a preferred manner, the surface structure extends in the circumferential direction to achieve blockage in the circumferential direction, i.e. in the turning direction of the screw.

Preferred embodiments provide that the surface structure is shaped as longitudinal grooves, serration, fluting or the like. It is also feasible to produce the surface structure by surface roughening.

In a preferred embodiment, the longitudinal grooves or the serrations are formed as saw-tooth serrations. Therein, each saw-tooth of the serration has a steep and a flat flank. To achieve a blocking effect in the screwing-in direction of the screw, the flat flank rises in the screwing-in direction of the bone screw. Screwing-in of the bone screw is thus relatively easy and the steep flank of a saw-tooth of the serration prevents unscrewing thereof.

The blocking effect can be optimized in that the screw head is provided with a surface structure which supports the blocking effect. The screw head can be provided in particular with grooves or the like extending in the longitudinal direction. Saw-tooth serration is also feasible.

Further advantages, features and details of the invention can be extracted from the following description which describes in detail a particularly preferred embodiment with reference to the drawing. The features shown in the drawing and mentioned in the claims and in the description can thereby be essential to the invention either individually or collectively in any arbitrary combination.

DESCRIPTION OF THE PREFERRED EMBODIMENT

Figure 1:
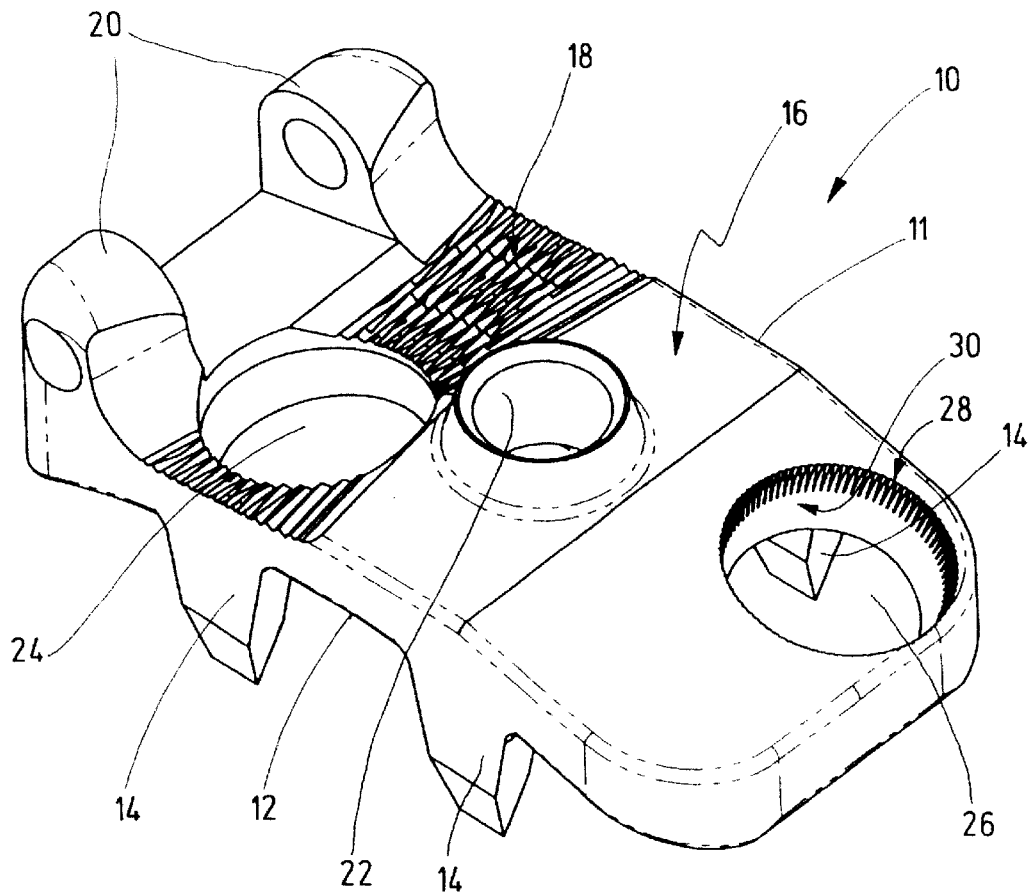
FIG. 1 shows a perspective view of a bone plate in accordance with the invention.

FIG. 1 shows a basic body 11 of a bone plate 10 which comprises, on its lower side 12 facing e.g. a vertebra, anchoring wedges 14 which are hammered into the bone. The basic body 11 is then supported with its lower side 12 on the surface of the bone. The basic body 11 comprises, on its upper side 16, a receiving area 18 into which a fixation rod (not shown) is inserted. This fixation rod is fixed by means of a lid pivotably fixed to a hinge 20 on the basic body 11 in that the lid is pivoted onto the fixation rod and e.g. held by means of a screw screwed into a threaded bore 22. The basic body 11 furthermore comprises two openings 24 and 26 into which bone screws are inserted which are, in turn, screwed into the bone. In this fashion, the basic body 11 is fixed to the bone.

The opening 26 has a spherical cap shape to permit reception of a spherical screw head. The area of the opening 26 facing the upper side 16 is thereby substantially steep and the area of the opening 26 facing the lower side 12 is slightly slanted.

Figure 2:
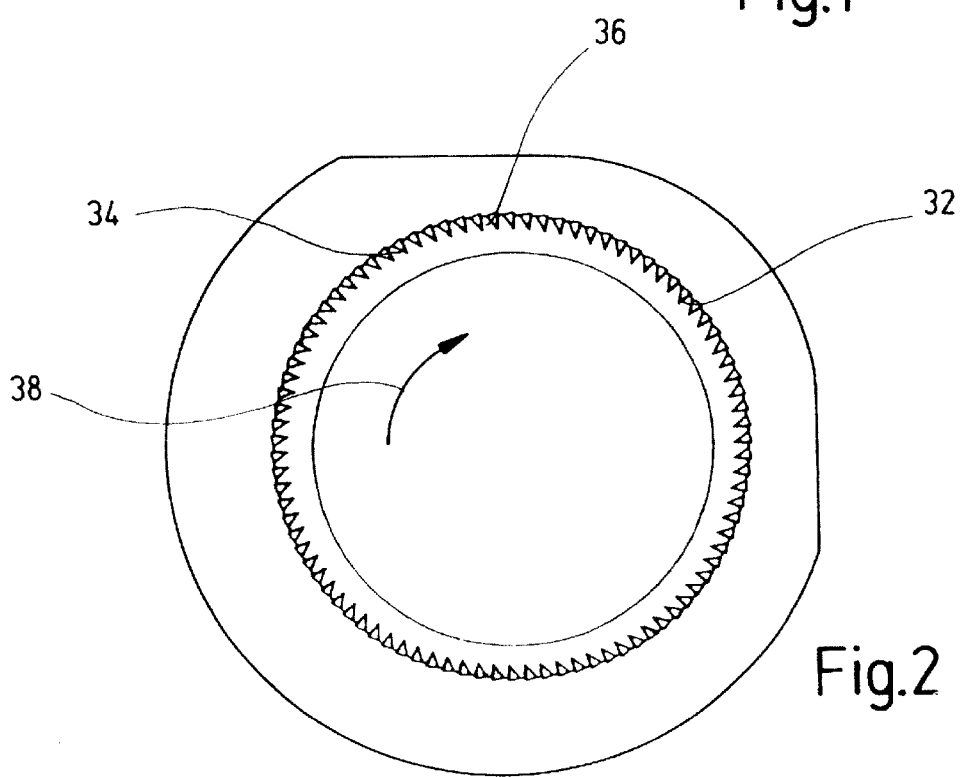
FIG. 2 shows a section of the bone plate showing, in top view, an opening comprising a surface structure.

The opening 26 has a surface structure 28 in its upper area, i.e. the area facing the upper side 16. Due to this surface structure 28, the opening 26 has, on its inner surface 30, not a smooth but a structured surface. This surface structure 28 is serrated 32 as shown in FIG. 2. This saw-tooth serration 32 comprises a flat flank 34 and a steep flank 36. The flat flank 34 is disposed such that it rises radially in the screwing-in direction (arrow 38). This facilitates screwing-in of the bone screw since the blocking effect in this screwing-in direction 38 is substantially less than in the unscrewing direction in which the steep flank 36 rises in a radial direction. The steep flank 36 thus exerts its blocking effect in the unscrewing direction and thus prevents automatic unscrewing of the bone screw or loosening of the bone screw in the bone. After screwing in, the screw head of the bone screw is anchored in the opening 26 in positive engagement.

The opening 24 may, of course, also be provided with a surface structure 28 of this type. The screw head may be provided partially or along its entire outer periphery with a surface structure, in particular with saw-tooth serrations, which are oriented in correspondence with the saw-tooth serrations 32 of the surface structure 28 of the opening 26.

We claim:

1. A bone plate for osteosynthesis using bone screws and a fixation rod, the bone plate comprising:

means for mounting a lid; and a plate-shaped basic body, said basic body having a first opening for accepting a first bone screw to attach the bone plate to bone, said first opening having a surface structure cooperating with a head of the first bone screw, wherein said surface structure is confined to an area of said first opening facing away from the bone, said basic body also having a second opening for accepting a second bone screw to attach the bone plate to bone, said second opening disposed within a region of the bone plate structured for accepting the fixation rod, whereby the fixation rod covers said second opening and the second bone screw following completion of an osteosynthesis procedure.

2. The bone plate of claim 1, wherein the bone is a vertebra.

3. The bone plate of claim 1, wherein the opening is circular.

4. The bone plate of claim 1, wherein said surface structure extends along an entire inner periphery of said opening.

5. The bone plate of claim 1, wherein said surface structure extends in a peripheral direction.

6. The bone plate of claim 1, wherein said surface structure has a blocking effect on the head of the bone screw.

7. The bone plate of claim 1, wherein said surface structure comprises at least one of longitudinal grooves, serrations and fluting.

8. The bone plate of claim 7, wherein said surface structure comprises saw-tooth serrations.

9. The bone plate of claim 8, wherein each saw tooth of said saw-tooth serrations comprises a steep flank and a flat flank.

10. The bone plate of claim 9, wherein said flat flank rises in a screwing-in direction of the bone screw.

11. The bone plate of claim 1, wherein said surface structure cooperates with a surface structure of the head of the screw.

12. The bone plate of claim 11, wherein said surface structure and said surface structure of the head of the screw cooperate to have a blocking effect in a turning direction of the bone screw.

13. The bone plate of claim 12, wherein said turning direction is an unscrewing direction.

14. The bone plate of claim 1, wherein said opening has a first region having a first slant relative to a vertical axis of the screw, said first region extending from a first side of said opening facing the bone, said opening also having a second region disposed adjacent to said first region and extending from said first region towards a second side of said opening facing away from the bone, said second region having a second slant relative to the vertical axis of the screw which is substantially larger than said first slant.

15. The bone plate of claim 14, wherein said surface structure is confined to said second region.

16. The bone plate of claim 15, wherein the screw positively engages said first region and frictionally engages said second region when the bone plate is attached to the bone.

* * * * *